United States Patent [19]

Wrighton et al.

[11] Patent Number: 4,717,673
[45] Date of Patent: Jan. 5, 1988

[54] MICROELECTROCHEMICAL DEVICES

[75] Inventors: Mark S. Wrighton, Winchester, Mass.; Henry S. White, Jr., Minneapolis, Minn.; James W. Thackeray, Cambridge, Mass.

[73] Assignee: Massachusetts Institute of Technology, Cambridge, Mass.

[21] Appl. No.: 798,263

[22] Filed: Nov. 19, 1985

Related U.S. Application Data

[63] Continuation-in-part of Ser. No. 674,410, Nov. 23, 1984.

[51] Int. Cl.[4] .................. G01N 27/22; G01N 27/26
[52] U.S. Cl. ..................... 436/68; 204/290 F; 204/235; 324/61 R; 350/357; 422/68; 422/90; 422/98; 436/151; 436/138; 436/163; 436/806; 435/291
[58] Field of Search ............. 350/357; 422/90, 98, 422/97, 68; 436/151, 806, 138, 163; 324/438; 204/78, 433, 435, 290 F, 291; 435/291

[56] References Cited

U.S. PATENT DOCUMENTS

| | | | |
|---|---|---|---|
| 3,999,122 | 12/1976 | Winstel | 422/98 |
| 4,350,660 | 9/1982 | Robinson et al. | 422/90 |
| 4,439,302 | 3/1984 | Wrighton et al. | |
| 4,442,422 | 4/1984 | Murata et al. | 422/98 |
| 4,444,892 | 4/1984 | Malmros | 436/151 |
| 4,461,691 | 7/1984 | Frank | 204/78 |
| 4,473,695 | 9/1984 | Wrighton et al. | |
| 4,557,978 | 12/1985 | Mason | 73/649 |
| 4,560,534 | 12/1985 | Kung et al. | 422/98 |
| 4,571,029 | 2/1986 | Skotheim et al. | 350/357 |
| 4,571,543 | 2/1986 | Raymond et al. | 422/98 |

OTHER PUBLICATIONS

White, Henry S., Gregg P. Kittlesen and Mark S. Wrighton, "Chemical Derviatization of an Array of Three Gold Microelectrodes with Polyprrole: Fabrication of a Molecule–Based Transistor", *J.Am.Chem.Soc.*, 106, 5375–5377 (1984).

White, Henry S., Gregg P. Kittlesen and Mark S. Wrighton, "Chemical Derivatization of Microelectrode Arrays by Oxidation of Pyrrole and N–Methylpyrrole: Fabrication of Molecule–Based Electronic Devices", *J.Am.Chem.Soc.*, 106, 7389–7396 (1984).

*Primary Examiner*—Michael S. Marcus
*Attorney, Agent, or Firm*—Patrea L. Pabst

[57] ABSTRACT

Very stable, polymer-based electrochemical devices, formed by polymerization of thiophene or a derivative such as 3-methylthiophene which is durable in an aqueous electrolyte over a wide pH range, which respond rapidly to chemical or electrical signals, are disclosed. In one embodiment, the device functions as an extremely sensitive sensor which measures changes in chemical concentration or pH. For example, a poly-3-methylthiophene-based device is sensitive to as little as $8 \times 10^{-16}$ moles of an oxidant which reversibly interacts with the polymer, including gas phase oxidants such as $I_2$. In a variation of the polymer-based device, a catalyst such as a noble metal or an enzyme, is dispersed on or within the conducting polymer matrix so that the device is responsive to chemicals such as $H_2$ and $O_2$ which the polymer would otherwise respond very slowly to. In a second embodiment, a polymer-based electrochromic device consists of polymer-coated microelectrodes which are individually addressed. Very high resolution is achieved by separating the microelectrodes by distances on the order of 10,000 Angstroms. In still another embodiment, the polymer-based device functions as a capacitor with an energy density as high as 200-300 $J/cm^3$ which can operate at frequencies as high as 100 Hz. Large polymer-based capacitors are useful for storage of solar energy or as automobile batteries. Microcapacitors may be incorporated into conventional integrated circuit designs.

19 Claims, 16 Drawing Figures

MICROELECTROCHEMICAL DEVICES

The Government has rights in this invention by virtue of Contract No. N0014-84-K-0553 and Contract No. N00014-84-K-0291 from the Office of Naval Research.

BACKGROUND OF THE INVENTION

This application is a continuation-in-part of U.S. Ser. No. 674,410 entitled "Molecule-Based Microelectronic Devices" filed Nov. 23, 1984 by Mark S. Wrighton, Henry S. White and Gregg P. Kittlesen.

Several types of microelectronic devices including diodes, transistors, sensors, surface energy storage elements and light-emitting devices were disclosed in U.S. Ser. No. 674,410 entitled "Molecule-Based Microelectronic Devices". These devices are fabricated using conventional masking and photolithography techniques to functionalize microelectrodes, formed by deposition of metal on insulating substrates such as silicon dioxide, with polymers whose physical properties change in response to chemical signals.

The primary difference between these devices and conventional solid state microelectronic devices is that they are responsive to chemical input. An important advantage of these devices over conventional macroscopic chemically reactive devices is that the disclosed devices can be readily incorporated into microelectronic systems which are responsive to electrical input. Other advantages of these devices include sensitivity and low power requirements.

It is an object of the present invention to provide polymer-based microelectronic devices with increased durability in an aqueous solution which are sensitive sensors for pH, hydrogen, oxygen, and other chemicals.

It is a still further object of the present invention to provide redox polymer-based microelectronic devices which rapidly and reproducibly amplify very small electrical or chemical signals.

It is another object of the present invention to provide redox plymer-based electronic devices which exhibit "metallic behavior" or a linear relationship between charge and potential over a wide range of pH and applied voltage.

It is a further object of the present invention to provide polymer-based, high density capacitors with a rapid discharge rate which are useful in automobiles, in computers, and for storage of solar energy.

It is a still further object of the present invention to provide polymer-based microcapacitors which can be incorporated into conventional integrated circuitry.

It is another object of the invention to provide polymer-based electrochromic devices with very high resolution, stability and rapid response.

SUMMARY OF THE INVENTION

Three embodiments of a thiophene or thiophene derivative polymer-based device are disclosed: a transistor-like device which amplifies small chemical signals such as changes in chemical concentration or pH, a high energy density capacitor, and an electrochromic device.

The first embodiment of the device is a polymer-based microelectrochemical sensor which is durable in an aqueous electrolyte over a wide pH range. The polymer is grown by the oxidation of thiophene or a thiophene derivative such as 3-methylthiophene and deposited on closely spaced gold or platinum microelectrodes. A pair of poly-3-methylthiophene-connected microelectrodes, for example, functions as a transistor, with one electrode serving as a "source" and the other as a "drain". The "source" electrode is referenced to the electrolyte solution which acts as a "gate". Conductivity of the poly-3-methylthiophene changes more than $10^8$ depending on the potential. Power amplification of a factor of about 1000 is possible at frequencies of 10 Hz. The device is turned on or off depending on the state of oxidation of the polymer. The device described responds to less than $10^{-15}$ moles of oxidant.

In a variation of this embodiment, the transistor is made responsive to chemical input via a catalyst such as a noble metal or an enzyme which is dispersed on or within the polymer matrix. A metal catalyst such as platinum makes the device useful as a very stable hydrogen or oxygen sensor which exhibits highly reproducible, significant responses to changes in concentration. Due to the small size, stability in an aqueous electrolyte, and reproducibility or response to a small chemical signal, this device has medical applications, for example, for use in monitoring blood pH and oxygen in a patient. Inclusion of an enzyme such as glucose oxidase as a catalyst provides a means for sensing the concentration of the enzyme substrate or the level of activity of the enzyme in the aqueous solution surrounding the device.

The second embodiment of the device is a high energy density capacitor formed from a conducting polymer. Due to the large effective internal surface area of the conducting polymer, about $10^4$ more charge per unit of projected area may be obtained when the polymer is 1.5 microns thick than for a smooth platinum electrode. Useful polymers include poly-3-methylthiophene since it has a large capacity ($1.9 \times 10^2$ F/cm$^3$), exhibits a linear relationship between charge and potential over a large potential range, can operate at a high frequency, and is durable in aqueous electrolyte. The capacitor may be constructed sufficiently large enough for use as a storage device for solar energy or small enough to put into an integrated circuit. The discharge rate is high enough to make the device useful as a car battery and has the advantage that it can be repeatedly 100% discharged and recharged.

The third embodiment is a very stable, rapidly responding electrochromic device constructed by individually derivatizing microelectrodes with the polymer, where high resolution is achieved by spacing the electrodes as closely as 10,000 Angstroms. The device is constructed using conventional masking and photolithography techniques to form the microelectrodes. Electrochemical deposition of polymer can be effected to give individually addressable polymer-coated microelectrodes that are not connected by the conducting polymer. The device is then completed by putting the polymer-coated microelectrodes in contact with an electrolyte and including a counter-electrode and transparent cover.

DETAILED DESCRIPTION OF THE INVENTION

Polymer-based electrochemical devices are produced by anodic deposition of a polymer formed from thiophene, or a derivative of thiophene such as 3-methylthiophene, onto a gold or platinum electrode surface. Microelectrochemical devices are fabricated using conventional masking and photolithography techniques, as described in U.S. Ser. No. 674,410 filed Nov. 23, 1984 by Wrighton et al. For example, poly-3-methylthiophene is grown onto microelectrode surfaces approximately 50 microns long, 1–2 microns wide, 0.1 microns high and separated by approximately 1 micron (10,000 Angstroms) by oxidizing 3-methylthiophene in $CH_3CN$/0.1 M [$n$-$Bu_4N$]$ClO_4$ solution. The typical procedure involves cycling at 200 mV/S the potential of an electrode to be derivatized between 0.0 V and +1.8 V vs. SCE in the presence of 50 mM 3-methylthiophene. The deposited polymer exhibits a cyclic voltammetry wave with a peak at about +0.7 V vs. SCE, which can be used to gauge the amount of deposited polymer. In derivatizing a microelectrode array, only those electrodes to be derivatized are cycled and those not to be derivatized are held at a negative potential, −1.0 V vs. SCE, to preclude growth of the poly-3-methylthiophene. A number of different devices may be formed by varying factors such as size and relationship of electrodes, polymer composition and thickness, electrolyte composition, and applied potential. Polymers which are useful in the present invention include polymers of thiophene and thiophene derivatives such as 3-methylthiophene and 3,4-dimethylthiophene. Such polymers have the advantage of being durable in aqueous solution.

In one embodiment, a pair of closely spaced microelectrodes of a microelectrode array are fabricated using conventional microfabrication techniques. A pair of polymer-connected microelectrodes functions as a transistor where a transistor is defined as a material whose resistance can be adjusted by a chemical or electrical signal. Current between the two microelectrodes at a given potential difference, $V_D$, is varied as a function of the gate potential, $V_G$, of the polymer electrically connecting the electrodes. One of the electrodes is regarded as the "source" and the other as the "drain", with the source being referenced to the solution as a "gate" when the device is used to amplify an electrical signal.

Figure 1A:
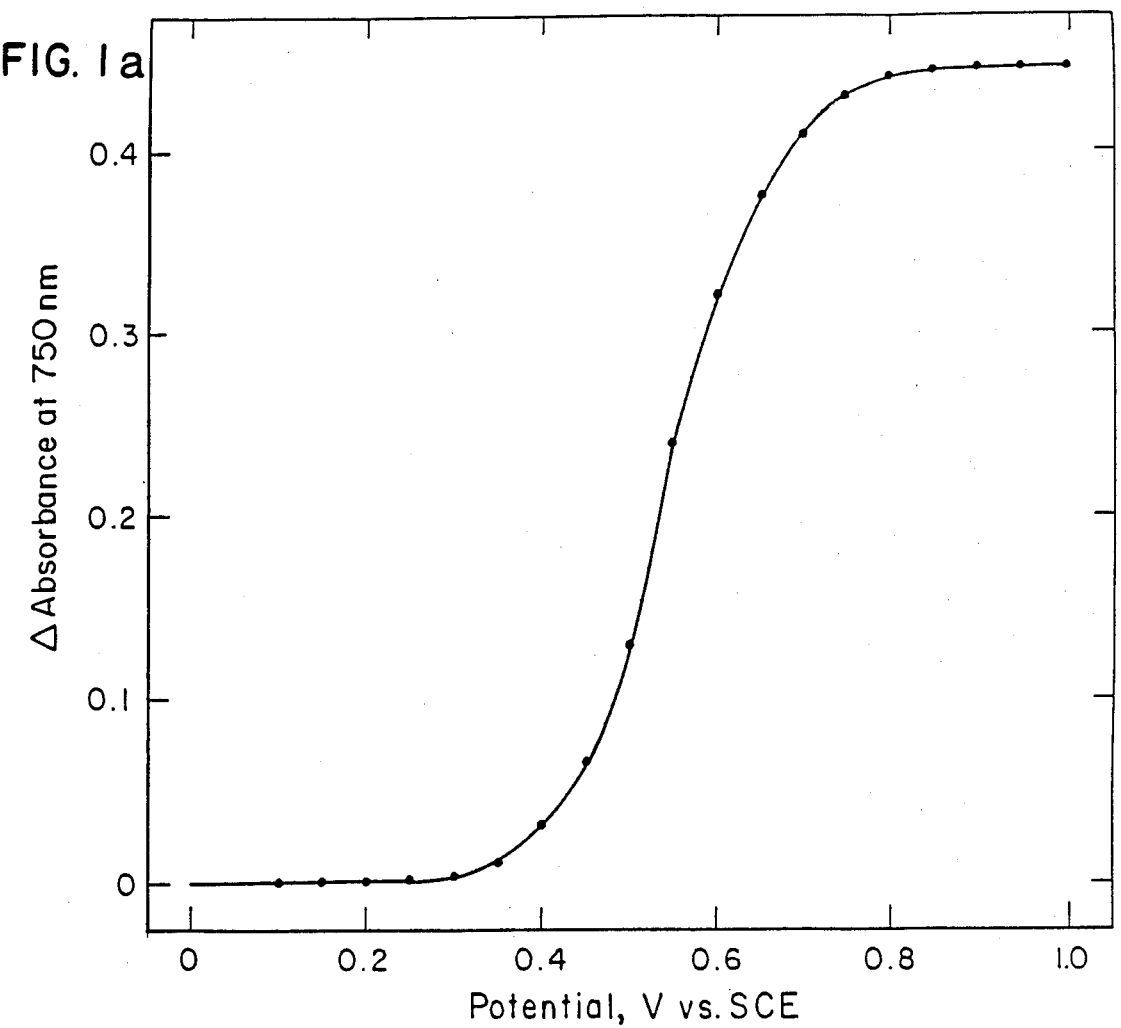
FIG. 1a is a graph of the change in absorbance at 750 nm accompanying the change of potential (V vs. SCE) of a partially optically transparent gold electrode coated with a 0.5 micron film of poly-3-methylthiophene in CH$_3$CN/0.1M [n-Bu$_4$N]ClO$_4$ electrolyte solution.
Figure 1B:
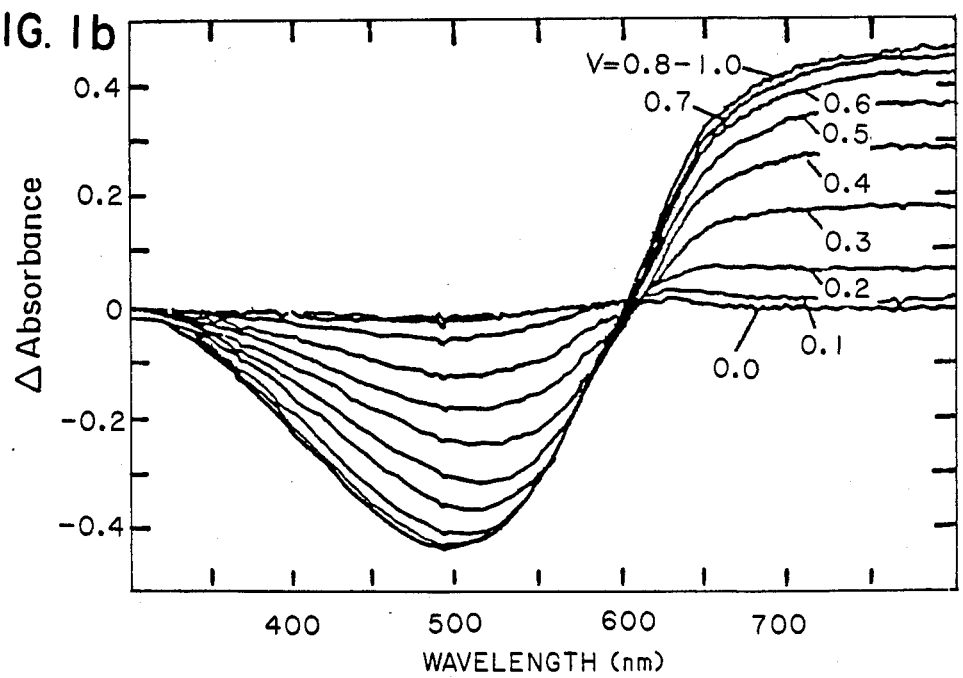
FIG. 1b is a graph of the change in absorbance vs. wavelength (nm) for the device of FIG. 1a at V vs. SCE=0.0, 0.1, 0.2, 0.3, 0.4, 0.5, 0.6, 0.7, and 0.8 to 1.0.

In a polymer-based device such as a poly-3-methylthiophene-based device, the polymer is the analogue of the channel of a solid state field effect transistor since the conductivity of the polymer changes by greater than $10^8$, depending on the potential. As shown in FIGS. 1a and 1b, the optical properties of the polymer, in the range of 300–800 nm, also depend on the electrical potential. The reduced material has an absorption maximum at 490 nm and the oxidized material has an absorption maximum at 750 nm. Changes in the optical density parallel the changes in resistance that occur as the potential of the polymer changes. The optical spectral changes in the near-UV/VIS, 300–800 nm, for the poly-3-methylthiophene transistor are substantial when the potential is varied between about +0.3 and +1.0 V vs SCE, as shown in FIG. 1b. Additional spectral changes occur in the near-IR region, 800–1500 nm, as the electrode potential is moved positive of +0.8 V vs SCE, however, the near-IR spectral changes do not reveal well-defined absorption bands.

Electrical signals can be amplified by a factor of about 1000 by poly-3-methylthiophene-based transistors at frequencies of 10 Hz. For electrical signals, when the gate voltage is negative, the "channel" is closed and there is a resistance of greater than $10^{10}$ ohms between microelectrodes. When the gate voltage is positive, the "channel" is open and the resistance between microelectrodes is approximately $10^2$ ohms. For chemical signals, a reductant acts to close the "channel" (resistance of the polymer is again greater than $10^{10}$ ohms) and an oxidant opens the "channel" (resistance of the polymer is approximately $10^2$ ohms).

Figure 2:
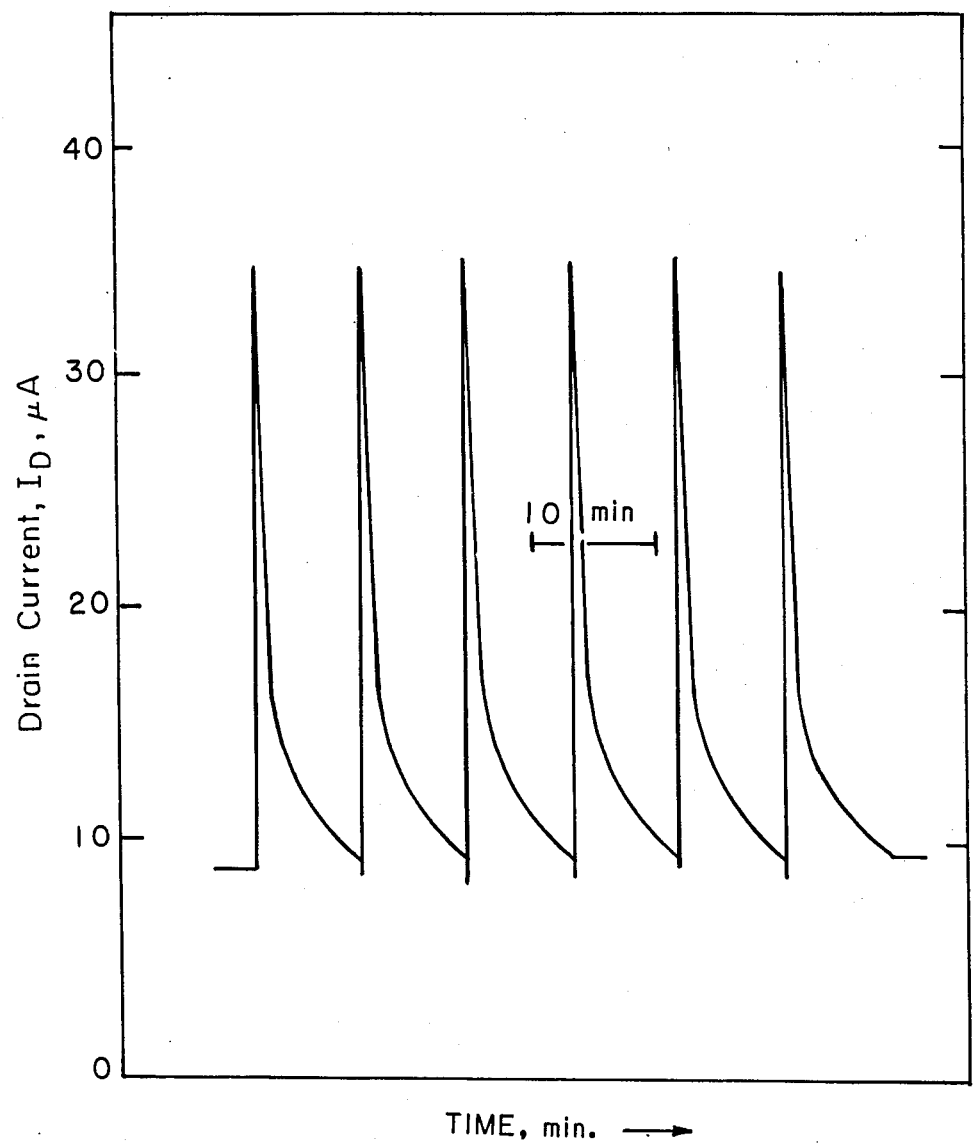
FIG. 2 is a graph of $I_D$ (microA) over time (minutes) of a poly-3-methylthiophene-based transistor at $V_D=0.1$ V and placed in the effluent stream (0.1M $NaClO_4$/0.05M $NaH_2PO_4$) of a Hewlett Packard Model 1084-b high pressure liquid chromatograph when 40 microliters of an aqueous solution of 0.01M $K_2IrCl_6$ was automatically injected every eight minutes into the electrolyte solution to provide a repetitive exposure to an oxidant, $IrCl_6^{2-}$, capable of turning on the transistor.

For example, a poly-3-methylthiophene-based electrochemical transistor placed in the effluent stream of a hewlett Packard high pressure liquid chromatograph reproducibly turns on or off in response to a chemical oxidant or reductant, respectively, introduced into the system via an automatic injector. Reproducible, repetitive chemical signals were delivered to a poly-3-methylthiophene-based transistor by placing the transistor in the effluent stream of the Hewlett Packard HPLC. The automatic injector was used to inject samples of an oxidant, $K_2[IrCl_6]$, or a reductant, $K_4[Fe(CN)_6]$, into a stream of aqueous electrolyte. A macroscopic Pt electrode was used as an indicator electrode to determine the solution potentials vs. time. FIG. 2 shows the response of the poly-3-methylthiophene-based transistor to six injections of $K_2IrCl_6$ in aqueous electrolyte. Testing was continued for 30 hours and the reproducibility was invariant. The device is "turned on" by the oxidant $IrCl_6^{2-}$, $E^{o'}(IrCl_6^{2-/3-}) = +0.68$ $V$ vs. $SCE$. In this example, the background impurity level of some reducing agent(s) in the solvent or electrolyte is apparently sufficient to swtich the device off. However, repetitive alternate injection of $IrCl_6^{2-}$ and $Fe(CN)_6^{4-}$ demonstrates rapid turn on/turn off cycles with no loss in reproducibility over many injections.

"Amplification" of the chemical signal is also possible. In the $IrCl_6^{2-}$ test, the number of oxidizing equivalents injected is $4 \times 10^{-7}$ moles and the integral of the $I_D$ vs. time plot for each injection shows that only $7.5 \times 10^{-9}$ moles of electrons pass between source and drain. However, the amount of $IrCl_6^{2-}$ that actually reaches the surface of the polymer is only a small fraction of the total $IrCl_6^{2-}$ injected, due to the geometry used in the experiments. A pair of "naked" electrodes in the eight-electrode array used to obtain the data in FIG. 2 can be used to determine the amount of $IrCl_6^{2-}$ that is available at the surface of the polymer-based transistor. The measurement involves injecting the $IrCl_6^{2-}$ $(4 \times 10^{-7}$ moles) and measuring the current corresponding to the reduction of $IrCl_6^{2-}$ to $IrCl_6^{3-}$ at the naked electrodes held at 0.0 V vs. SCE. The integral of the reduction current vs. time plot, $3.2 \times 10^{-8}$ C, shows that $3.2 \times 10^{-13} \pm 20\%$ moles of $IrCl_6^{2-}$ are reduced on each injection. This means that only about $8 \times 10^{-5}\%$ of the injected $IrCl_6^{2-}$ actually reaches the transistor. Thus, the amplification of the chemical signal can exceed $2 \times 10^4$ using the poly-3-methylthiophene-based device. Assuming that the fraction of oxidant coming to the surface of the transistor is $8 \times 10^{-5}\%$, the device has been shown to respond to $8 \times 10^{-16}$ moles of the oxidant. With such an injection, reduction of the $IrCl_6^{2-}$ to $IrCl_6^{3-}$ at the two naked electrodes could not be detected with the equipment available. While the deposited poly-3-methylthiophene is typically used in an amount that requires about $10^{-12}$ moles of oxidizing equivalents to turn it completely on, some small fraction, less than $10^{-3}$, can give an easily measured change in $I_D$.

Figure 3:
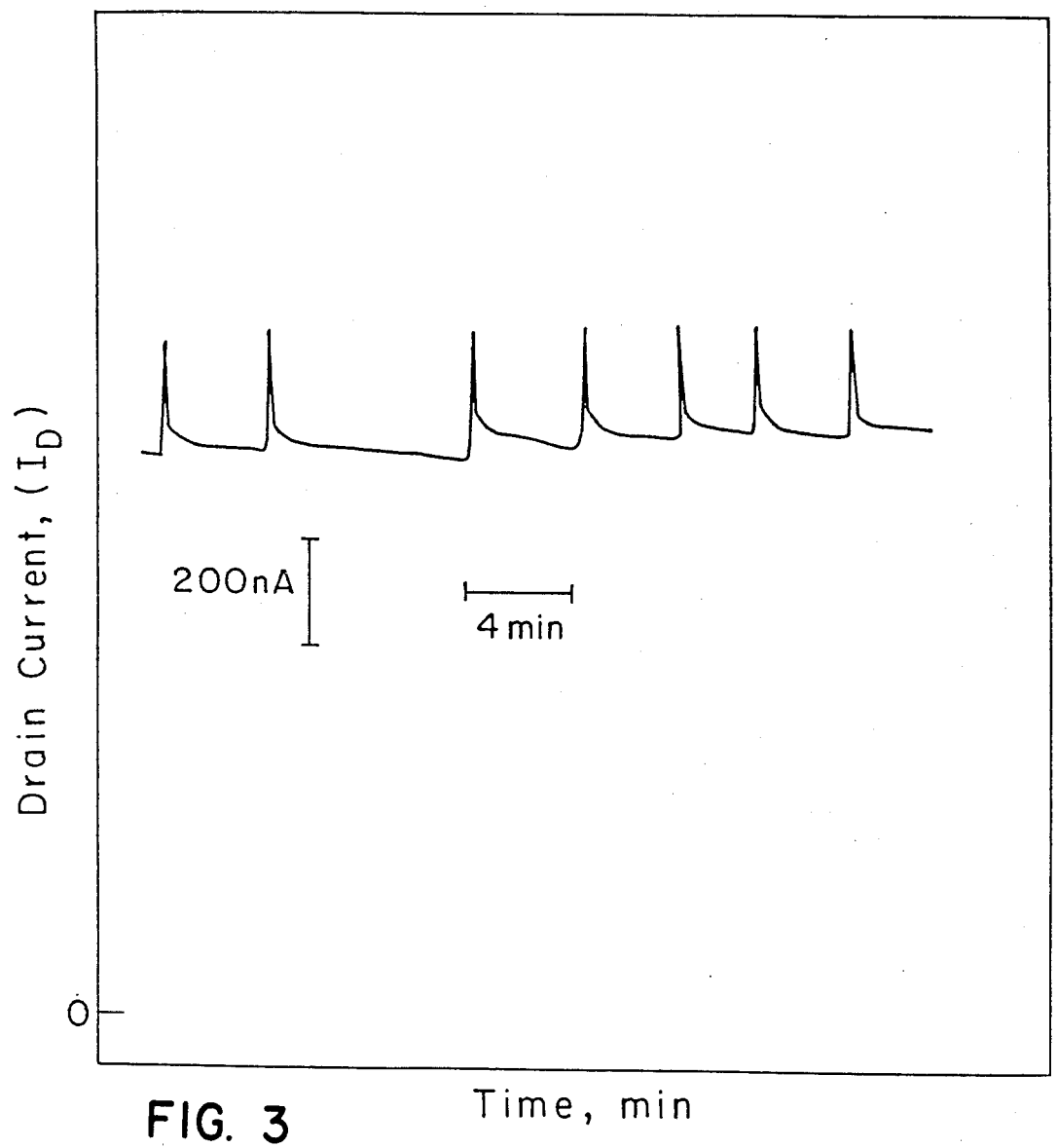
FIG. 3 is a graph of $I_D$ (nA) vs. time (minutes) for a poly-3-methylthiophene-based transistor at $V_D=0.1$ V for 0.3 micromole injections of $I_2$ vapor into an argon gas stream at a flow rate=2.0 ml/min.

The poly-3-methylthiophene-based device can be used to detect changs in oxidant or reductant concentrations in a gas phase as well as in a liquid electrolyte solution. For example, the device can be used to detect very low levels of $I_2$ in an inert gas such as argon. FIG. 3 demonstrates the extremely rapid, reversible response of a poly-3-methylthiophene based device located in a flowing stream of argon gas to injections of a small amount of oxidant, $I_2$, in the gas phase.

Cyclic voltammograms, as a function of sweep rate for a pair of adjacent, poly-3-methylthiophene-derivatized microelectrodes in $CH_3CN/0.1M$ [n-$Bu_4N$]$ClO_4$, show that a microelectrode purposely not derivatized, but adjacent to derivatized microelectrodes, shows little or no electrochemical response characteristic of the immobilized poly-3-methylthiophene. The ability to derivatize one microelectrode and not another adjacent to it establishes that closely spaced (approximately 10,000 Angstroms) microelectrodes can be derivatized in a way that allows a very high resolution display. Electrochemical characterization, which can detect very small amounts, approximately one monolayer, or redox active material, substantiates SEM characterization of deriviatized microelectrode arrays that shows that the electrodes can be modified in a controlled fashion. Cyclic voltammetry establishes that two or more microelectrodes can be connected with poly-3-methylthiophene. The minimum amount of poly-3-methylthiophene that can connect two microelectrodes, fabricated of poly-3-methylthiophene using the method described in U.S. Ser. No. 674,410, is associated with a cyclic voltammogram that has an area corresponding to $10^{-8}$ C in a cyclic sweep between 0.0 and +0.8 V vs. SCE.

Figure 4A:
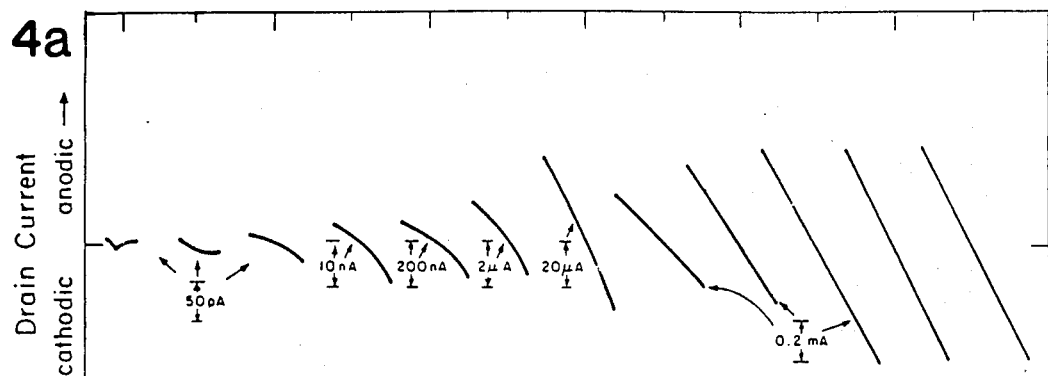
FIG. 4a is a graph of drain current potential curves (pA at 0.0 to 0.2 V vs. SCE, nA at 0.2 to 0.45 V vs. SCE, microA at 0.45 to 0.7 V vs. SCE, and mA at 0.7 to 1.1 V vs. SCE) as a function of the gate potential for a pair of poly-3-methylthiophene-connected microelectrodes in $CH_3CN$/0.1M [$n$-$Bu_4N$]$ClO_4$ when the potential of one of the microelectrodes is varied a small amount, approximately 20 mV, around the gate potential.
Figure 4B:
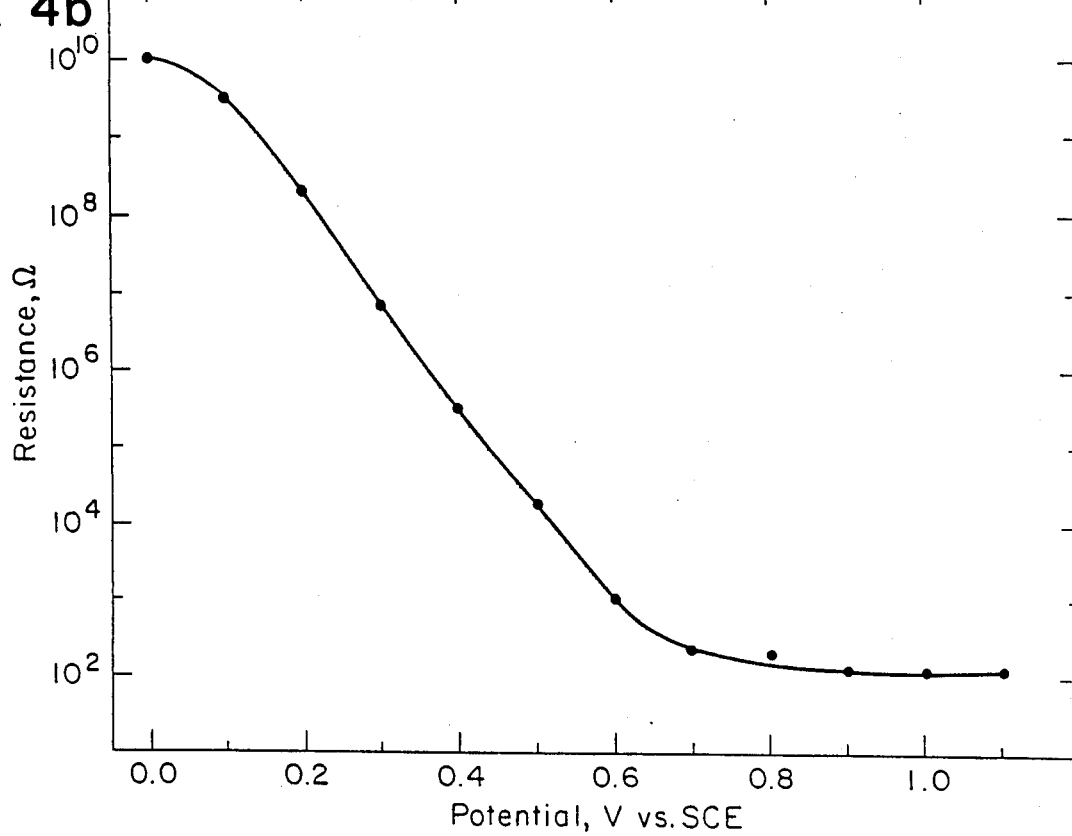
FIG. 4b is a graph of the resistance (ohms) between the two microelectrodes as a function of gate potential (V vs. SCE).

At a sweep rate of up to 500 mV/S, an ordinary, low conductivity redox polymer, such as polyvinylferrocene, that connects the microelectrodes at slow sweep rates of 5 mV/S, would behave as if the two microelectrodes are not connected: the area of the cyclic voltammogram for A and B driven together would be the sum of the areas for A and B alone. Steady state current-voltage data shows that charge can be passed from one microelectrode to a second, polymer-connected, microelectrode to assess the resistance of the polymer as a function of the potential of the polymer. Removal of a small amount of electrical charge from the poly-3-methylthiophene coatin two microelectrodes dramatically increases the conductivity, as shown in FIG. 4a. FIG. 4b gives representative data from studies of a pair of microelectrodes connected by poly-3-methylthiophene: the resistance between the two connected microelectrodes declines by greater than eight orders of magnitude upon a change in potential from 0.0 V to +0.8 V vs. SCE.

Figures 5A, 5B:
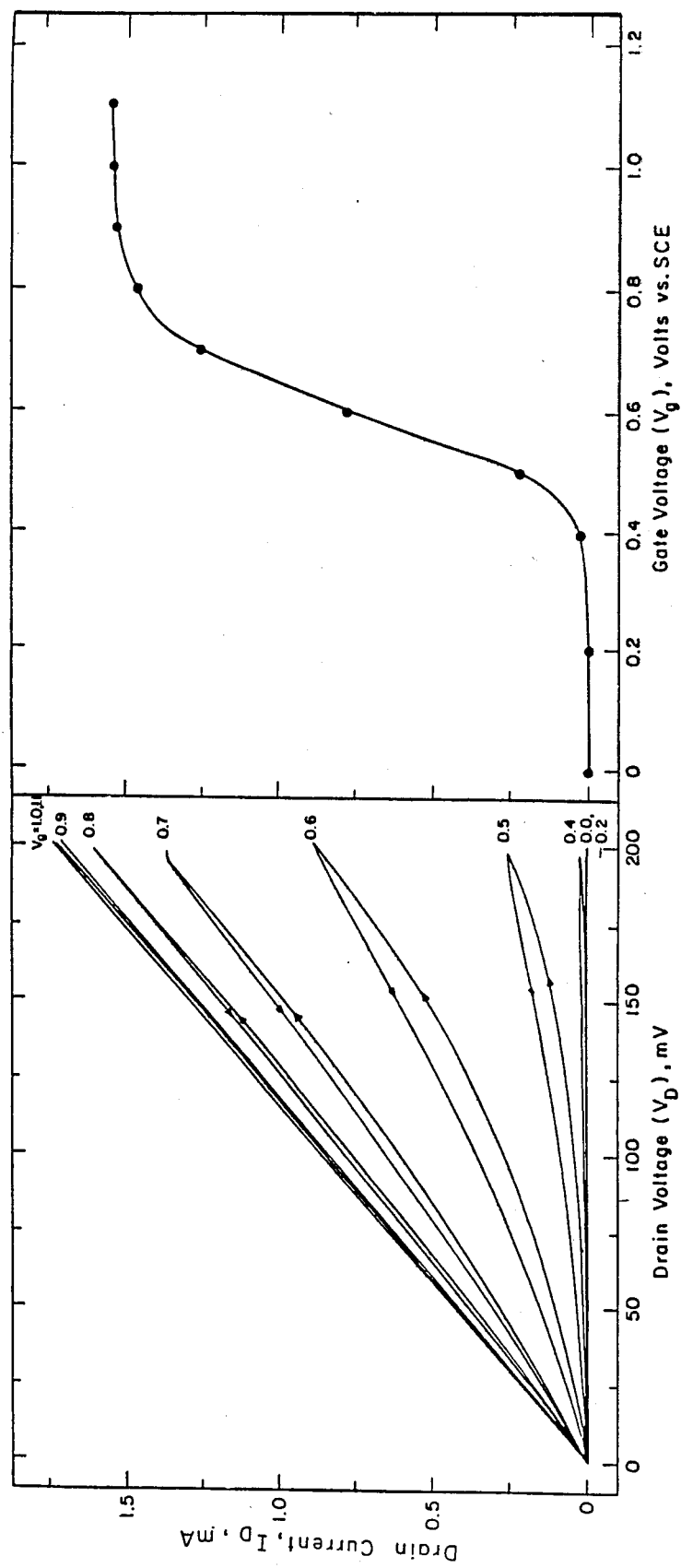
FIG. 5a is a graph of $I_D$ (mA) vs. $V_D$ (mV) at fixed $V_G$ (−0.2 to 1.0 V vs. SCE) for a poly-3-methylthiophene-coated microelectrode array.
FIG. 5b is a graph of $I_D$ (mA) vs. $V_G$ (V vs. SCE) for a poly-3-methylthiophene-coated microelectrode array at 5 mV/s.

To obtain the data in FIGS. 4a and 4b, one of the two microelectrodes is held at a potential, $V_G$, and the potential, $V_D$, of the other microelectrode is moved linearly in time plus or minus about 20 mV around the fixed potential of the first, while monitoring the current, $I_D$, that passes between the two microelectrodes. The current that passes through one electrode/polymer interface is equal in magnitude, but opposite in sign, to the current that passes through the other electrode/polymer interface. The resistance is taken to be the slope of the $I_D$ vs. $V_D$ plot at $V_D = 0$. FIG. 5a is a graph of the Drain Current v. Drain Voltage at fixed Gate potentials between $-0.2$ V and 1.0 V. FIG. 5b is a graph of Drain Current vs. Gate potential (0.0 to 1.2 V).

The "resistance" between adjacent, non-derivatized microelectrodes in $CH_3CN/0.1$ M [n-$Bu_4N$]$ClO_4$ is greater than $10^{10}$ ohms. The data in FIGS. 4 and 5 are for devices in CH$_3$CN/0.1M [n-Bu$_4$N]ClO$_4$. Such plots are typically used to characterize transistors. Similar resistance vs. potential plots are found in an aqueous electrolyte, pH=1 to 9; 0.1M LiClO$_4$ or 0.1M NaClO$_4$ or 0.1M HClO$_4$, with a maximum resistance at $-0.2$ V vs. SCE of about $8 \times 10^7$ ohms. The minimum resistance is nearly the same as in CH$_3$CN, about $10^2$ ohms. The potential "window" for non-Faradaic processes in H$_2$O is significantly less than in CH$_3$CN, due to the small decomposition potential for H$_2$O. It is important to note that the resistance changes in the poly-3-methylthiophene with variation in potential are reversible, provided the positive limit is less than $+1.4$ V vs. SCE in CH$_3$CN and less than $+0.8$ V vs. SCE in H$_2$O. More positive potentials result in irreversible oxidative degradation of the polymer.

The poly-3-methylthiophene has a maximum conductivity that is superior, by about one order of magnitude, to that found for polypyrrole in CH$_3$CN/[n-Bu$_4$N]ClO$_4$ and the total change in conductivity is larger for a given potential change. The polypyrrole is more difficult to drive to as low a conductivity as found for the poly-3-methylthiophene. The maximum conductivity of the poly-3-methylthiophene is estimated to be $10^2$ ohm$^{-1}$ cm$^{-1}$. There is a correlation of the potential dependence of optical, charging, and resistance properties of poly-3-methylthiophene.

Qualitatively, the characteristics of the poly-3-methylthiophene-based transistor device are similar to those for a polypyrrole-based device. However, three features of the poly-3-methylthiophene-based device are especially impressive. First, the poly-3-methylthiophene is rugged over a wider potential regime and is rugged in aqueous solutions. Second, the maximum slope of the $$I_D \text{ vs. } V_G \text{ plot, } \left.\frac{\partial I_D}{\partial V_G}\right|_{V_D \text{ fixed}}$$

is very large: 120 mS/mm of gate width. In the language of solid state devices, where the distance between source and drain of a field effect transistor (FET) is the gate length, the slope of the $I_D$ vs. $V_G$ plot is called the transconductance. The transconductance is 270 mS/mm of gate width for state-of-the-art Si/SiO$_2$/metal FET (Si MOSFET) where the gate length is 1400 Angstroms. In the example of a poly-3-methylthiophene transistor, the "gate length" is 1.2 microns, the separation between the two microelectrodes. The transconductance for the polymer-based device will be larger if the separation between the microelectrodes is smaller. The third feature of significance for the poly-3-methylthiophene-based device is the large maximum value of $I_D$. The typical maximum value for $I_D$ is about 1 mA at $V_G = 0.2$ V, significantly larger than for polypyrrole or polyaniline-based transistor devices. The large maximum value of $I_D$ is due to the poly-3-methylthiophene having superior conductivity. The large transconductance is due to the relatively sharp increase in conductivity with movement of the electromechanical potential of the polymer from negative to positive potentials.

There are two important differences between the microelectrochemical device of the present invention and traditional transistors. The first difference is that the channel thickness of a state-of-the-art MOSFET is much smaller than the thickness of the polymer. This results in the need for a relatively large amount of charge to turn on the microelectrochemical devices. A fraction of $10^{-7}$ moles of e$^-$/cm$^2$ must be withdrawn from the polymer to completely turn on the poly-3-methylthiophene-based device. In absolute terms, about $10^{-13}$ moles of e$^-$'s must be withdrawn to substantially turn on the devices. A Si MOSFET can be turned on with about $10^{-12}$ moles of e$^-$'s/cm$^2$ of gate area. The second difference is that, in using a redox polymer, such as a conducting polymer, as the "channel" material, the charge needed to turn on the device is associated with the movement of ionic species into polymer. The electrochemical conversion of poly-3-methylthiophene from insulating to conducting involves chemical changes, whereas the changes in current flow between source and drain in a solid state FET are a consequence of the movement of capacitive charge, not ion movement. As a result, the turn on/turn off rate of the polymer device will be slower than for solid state devices and the frequency of operation of the microelectrochemical device will be limited by oxidation/reduction times. Redox polymers, at thicknesses of several tenths of a micron, have been electrochemically driven between oxidized and reduced states at frequencies of the order of 10 Hz. The poly-3-methylthiophene-based microelectrochemical transistor can be turned on and off rapidly, on the one second time scale. In the example, the device is turned on, $V_G$ stepped from 0.0 V to $+0.9$ V vs. SCE, within 20–50 ms and turned off, $V_G$ stepped from $+0.9$ V to 0.0 V vs. SCE, within 20 ms.

Applying a sinusoidal change of $V_G$, negative limit=0.0 V and positive limit=$+0.9$ V vs. SCE, at 10 Hz, shows that substantial power gain can be realized with a poly-3-methylthiophene-based transistor. Under such conditions, the maximum gate current is about 1 microA while the maximum $I_D$ at $V_D=0.2$ V is about 1 mA. Substantial loss in power amplification occurs between 10 and 100 Hz under these conditions. When the device is driven with a sinusoidal $V_G$ between $+0.4$ V and $+0.9$ V vs. SCE, the response is better because the device is partially "on" at $+0.4$. Power amplification of about 1000 can be obtained at 10 Hz with the power in the gate circuit associated with the charge passed in the potential sweep between 0.0 V (fully off) and $+0.9$ V vs. SCE (fully on).

The poly-3-methylthiophene-based microelectrochemical transistor is durable in aqueous eletrolyte over a wide pH range, 0 to 12. At a $V_D$ of 0.1 V and $V_g = +0.5$ V vs. SCE, a nearly constant, and large, $I_D$ is found for a period of 6 h. During the 6 h, about 15 C of charge passes through each electorde/polymer interface, corresponding to about $15 \times 10^6$ C/cm$^2$. The devices have been demonstrated to undergo thousands of on-off cycles with no change in device performance.

The polymer may be chemically derivatized by inclusion of a catalyst, such as a noble metal which will equilibrate with the redox reagent of interest or an enzyme. For example, PtCl$_4^{2-}$ or any other reducible noble metal salt such as PdCl$_4^{2-}$ or PtCl$_6^{2-}$ can be reacted to deposit the metal on or within the polymer matrix. Other complexes known to those skilled in the art may also be used to achieve the same result. The number of metal particles, which are approximately 200 Angstroms in size, must be limited so that the polymer matrix continues to exhibit a substantial change in conductivity with change in potential. Enzymes may also be bound to the polymer matrix. Catalysts which are useful in the present invention include those which are both specific and which result in a measurable change to redox reagents of interest. One example of a useful enzyme is glucose oxidase for equilibrating the polymer with the glucose/oxygen system.

Figure 6:
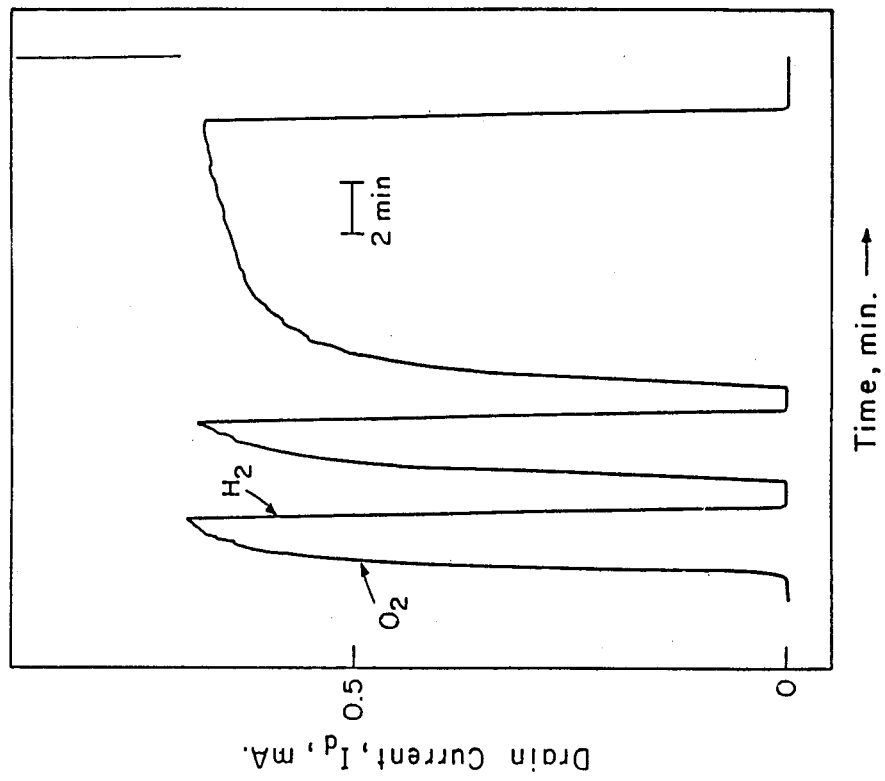
FIG. 6 is a graph of $I_D$ (mA) vs. time (minutes) for a poly-3-methylthiophene-Pt transistor upon alternate cycling of 1 atm of $O_2/H_2$ in 0.1 M $HClO_4/H_2O$ at $V_D=0.2$ V.

A platinum-catalyzed poly-3-methylthiophene based device was constructed by reducing $PtCl_6^{2-}$ to yield embedded elemental Pt(0) in highly dispersed form in the polymer matrix. Platinum provides a mechanism for inducing a change in conductivity of the polymer in response to changes in concentration of hydrogen or oxygen in the electrolyte. FIG. 6 is a graph of the drain current for a poly-3-methylthiophene-Pt transistor in response to alternate cycling of 1 atm $O_2/H_2$ in 0.1M $HClO_4/H_2O$ when $V_D$ is 0.2 V.

Figure 7:
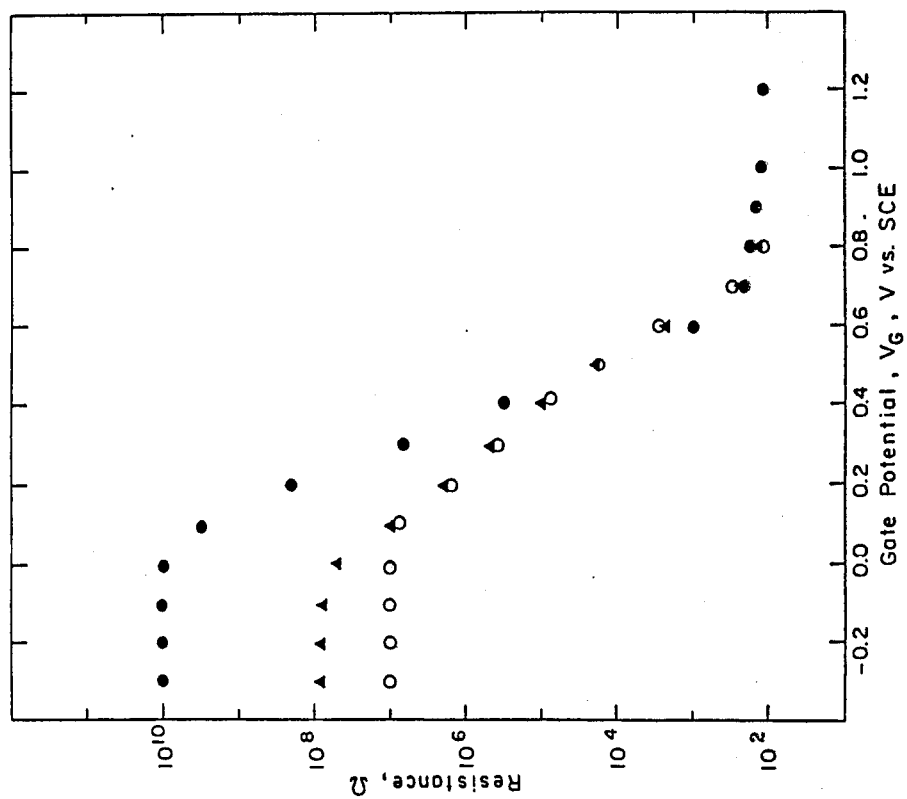
FIG. 7 is a graph of resistance (ohms) vs. gate potential, $V_G$, (V vs. SCE) for a poly-3-methylthiophene-based transistor in $CH_3CN$ and in an aqueous electrolyte, both before and after incorporation of Pt into the polymer.

FIG. 7 demonstrates that dispersion of Pt in the polymer matrix does not have any significant effect on the conductivity at a given gate potential when the device is in either $CH_3CN$ (line a) or an aqueous electrolyte (line b, before Pt deposition; line c, after Pt deposition).

Figure 8:
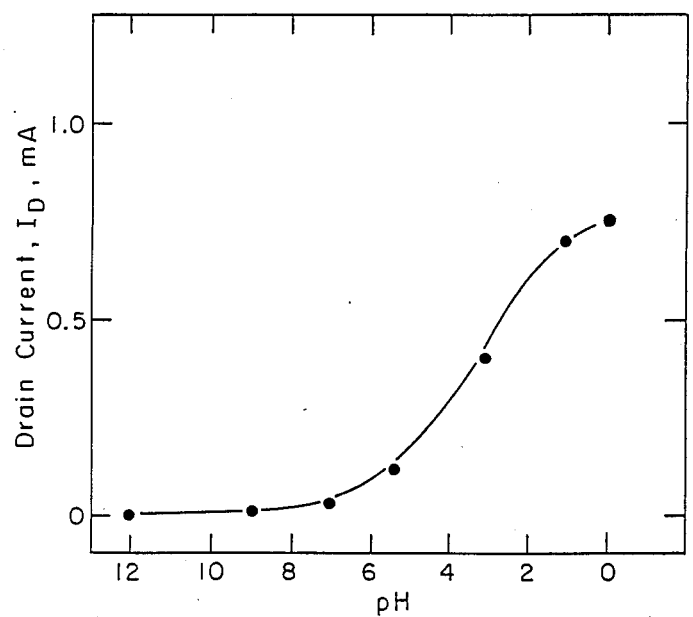
FIG. 8 is a graph of drain current, $I_D$, (mA) vs. pH for a poly-3-methylthiophene-Pt transistor under 1 atm $O_2$, $V_D=0.2$ V.
Figure 9:
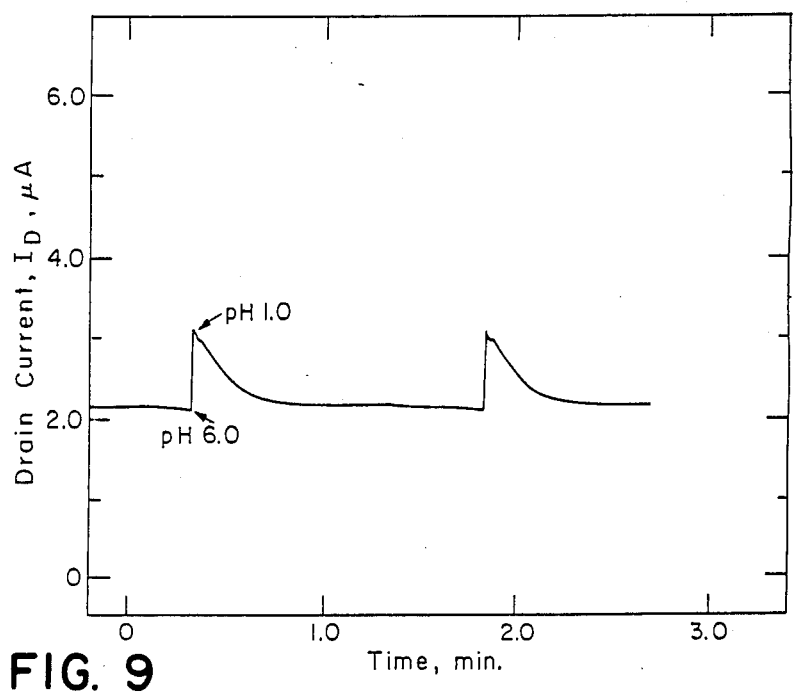
FIG. 9 is a graph of drain current, $I_D$, (microA) vs. time (minutes for a poly-3-methylthiophene-Pt transistor at $V_D=0.100$ V upon injection of one microliter 0.1M $HClO_4$ into an effluent stream of 0.1M $NaClO_4$, pH 6.0, at a flow rate of 2.0 ml/min.
Figure 10:
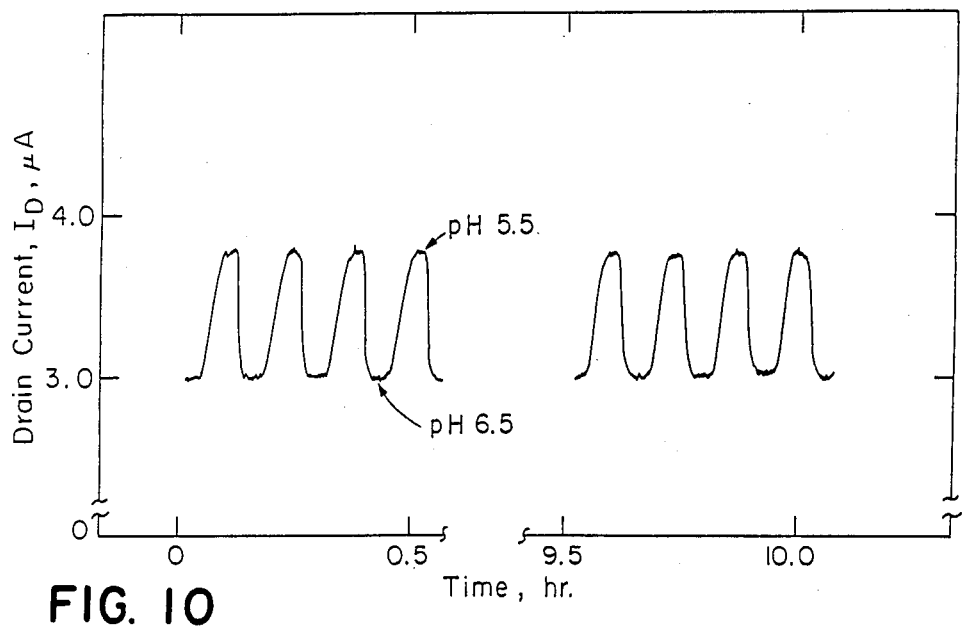
FIG. 10 is graph of drain current, $I_D$, (microA) vs. time (hours) for a poly-3-methylthiophene-Pt transistor at $V_D=0.2$ V upon alternate cycling of a pH 5.5/pH 6.5 effluent stream at a flow rate of 2.0 ml/min.

The poly-3-methylthiophene-Pt transistor can be used as a pH sensor in aerated solutions, as shown by FIG. 8. As demonstrated in FIG. 9, the response time to a change in pH is extremely rapid, on the order of a few seconds and is significant. This response is extremely reproducible and table over time, as shown in FIG. 10.

Figure 11A:
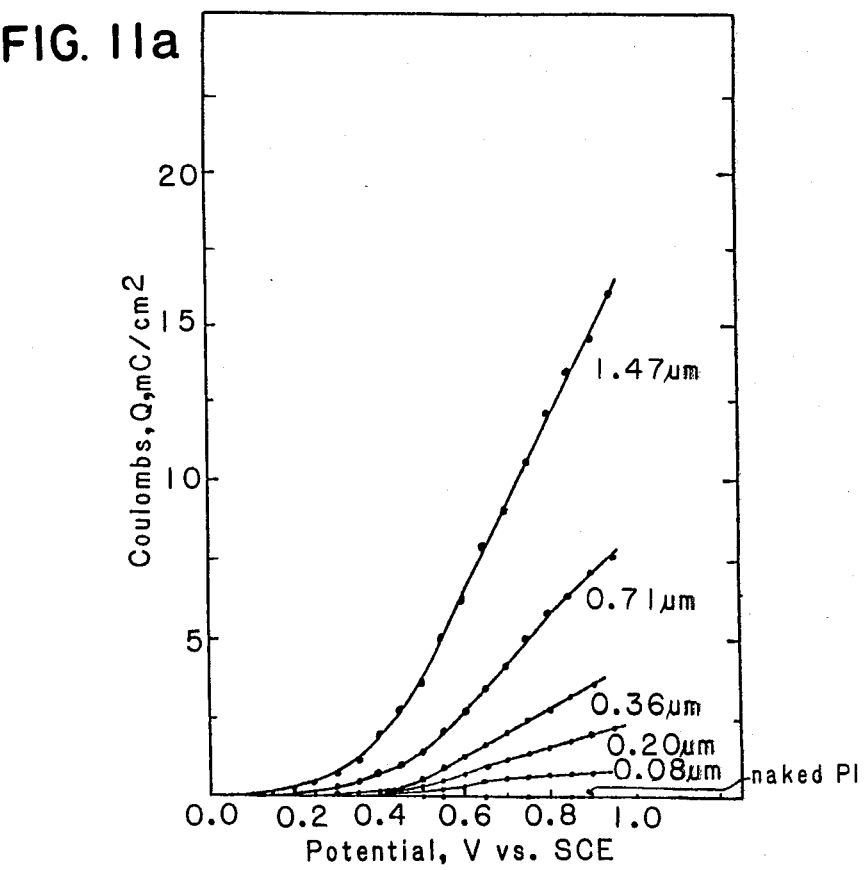
FIG. 11a is a graph of the charge passed ($mC/cm^2$) for poly-3-methylthiophene on platinum electrodes in $CH_3CN$/0.1 M [$n$-$Bu_4N$]$ClO_4$ from a given potential (V vs. SCE) to 0.0 V vs. SCE as a function of the thickness (microns) of the poly-3-methylthiophene anodically grown onto the platinum electrodes.
Figure 11B:
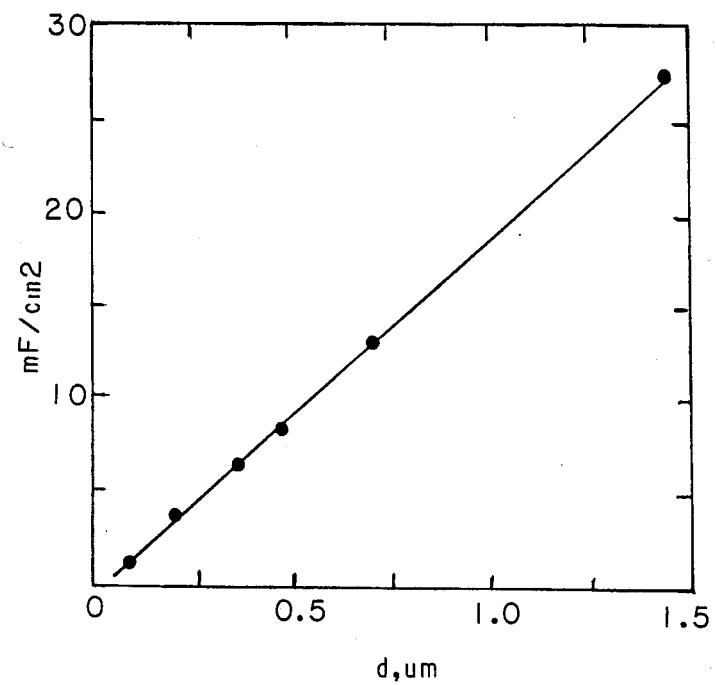
FIG. 11b is a graph of the capacitance ($mF/cm^2$) vs. thickness (microns) of the polymer, in the straight line portion of the $mC/cm^2$ potential plots, positive of +0.5 V vs. SCE, where the slope is $1.9 \times 10^2$ Farads/$cm^3$.

A capacitor or device for storing electrical energy, can be produced by coating at least one of two electrodes with a thiophene (or thiophene derivative)-based polymer. The electrodes must be separated by an ionically conducting separator. The "charging" of a 1.5 micron thick film of poly-3-methylthiophene involves about $10^4$ times more charge per unit of projected area than a smooth platinum electrode due to the large effective internal surface area of the conducting polymer. Polymers used as the basis for electrochemical "double layer" capacitors must have a high capacitance, exhibit a linear relationship between charge and potential over a large potential range, operate at high frequency, and be durable in aqueous electrolyte. For example, as shown in FIGS. 11a and 11b, poly-3-methylthiophene has a capacity of $1.9 \times 10^2$ F/cm$^3$, exhibits a linear relationship between charge and potential at potentials greater than $+0.5$ V vs. SCE, and has high conductivity at a potential greater than $+0.5$ V vs. SCE, approximately $10^2$ ohm$^{-1}$ cm$^{-1}$. Charge can be withdrawn from the poly-3-methylthiophene beyond $+0.8$ V vs. SCE. As the data in FIG. 11 show, the total charge withdrawn from the polymer as a function of potential appears to be linear with potential in a potential regime where the visible region of the optical spectrum is nearly constant (FIG. 1).

FIG. 11b shows that poly-3-methylthiophene has a remarkable capacitance: $1.9 \times 10^2$ F/cm$^3$. FIG. 11b shows a linear plot of mF/cm$^2$ vs. polymer thickness where the slope of the straight line gives the capacitance of the film. The individual data points for the various thicknesses shown in FIG. 11a are from the slopes of the plots of charge vs. potential for potentails more positive than $+0.5$ V vs. SCE, where the charge vs. potential appears to be quite linear. For comparison, the charge vs. potential for a smooth Pt electrode is included in FIG. 11b. This charge is the double layer charging associated with the metallic electrode and the capacitance is about 10 microF. The poly-3-methylthiophene-coated electrodes have a large capacitance, and, in the potential regime more positive than $+0.5$ V vs. SCE, the poly-3-methylthiophene appears to behave as a "metallic" electrode with very high internal surface area giving rise to a double layer capacitor of extraordinary capacitance, on the order of 200 J/cm$^2$.

Redox polymers such as polyvinylferrocene or polyviologen have of the order of 1-3 moles of monomer units per cubic centimeter of polymer but react too slowly to be useful in a high frequency capacitor when the thickness of the polymer is large. For a one-electron change per monomer, the capacity is about $1-3 \times 10^2$ F/cm$^3$. Poly-3-methylthiophene and, presumably, other "conducting" polymers, are distinctive in that there is a more or less well-defined and wide potential regime where the charge vs. potential is linear. For polyvinylferrocene and polyviologen, the charge vs. potential would not be linear over a wide potential regime since the redox subunits comprising the polymer do not interact strongly and charge is added or extracted from the polymer at potentials with about 100 mV. of the formal potential. The potential region between about $+0.1$ and $+0.5$ V vs. SCE for poly-3-methylthiophene is analogous to the behavior of polyviologen or polyvinylferrocene. However, as the potential is moved more positive, the poly-3-methylthiophene becomes "metallic" in behavior. The conclusion that the poly-3-methylthiophene becomes metallic for potentials positive of $+0.5$ V vs. SCE is supported by the dramatic increase in conductivity upon electrochemical oxidation.

Defining "metallic" as producing a linear plot of charge vs. potential, a polymer having a variety of redox subunits with closely spaced redox potentials could be regarded as "metallic". For example, a polmer derived from ring-substituted derivatives of vinylferrocene could have a linear charge vs. potential plot over a wide potential range. However, unlike poly-3-methylthiophene, such a polymer would not be expected to have high conductivity because the individual redox subunits do not interact strongly: the polyvinylferrocene has a "conductivity" some $10^6$ times lower than poly-3-methylthiophene. Such low conductivities mean that a capacitor based on these materials would have low charbe/discahrge rates. The high conductivity of poly-3-methylthiophene allows high frequency operation. It is important to note that while polyvinylferrocene and other conventional redox polymers do have some features in common with conducting polymers, there are important differences.

The potential of poly-3-methylthiophene cannot be moved positive without limit. Extraction of charge makes the polymer more and more positively charged and more and more reactive in electrolyte solutions. In dry $CH_3CN$, the films remain durable to at least $+1.4$ V vs. SCE. In $H_2O$, potentials positive of about $+0.8$ V vs. SCE lead to decomposition.

The amount of charge that can be withdrawn from a conducting polymer without adversely affecting the conductivity is a function of the polymer. For example, polyaniline shows a relatively small potential region of high conductivity compared to polypyrrole. Further, the change in conductivity with "doping" level can be a function of the polymer. These variations in properites can be exploited to produce unique microelectrochemical device characteristics.

The polymer-based capacitor has a number of potential uses. The rate of response and discharge rate are dependent on the thickness of the polymer. Response rate decreases as polymer thickness increases since the device responds as a function of movement of ionic species into the polymer. However, a large energy storage device, such as a capacitor for storing solar energy collected by photovoltaic cells, can be constructed by providing an electrode overlaid with polymer, an ionic conductor or separator, such as the paper used in making conventional electrolytic capacitors, another layer of polymer deposited on a second electrode and a sealed housing. When a suitable electrolyte solution, such as $Na^+SO_4{}^{2-}$, is injected between the two polymer layers and a voltage applied to the electrodes, charge is transferred. The length and width of the polymer-coated electrodes may be dimensioned as required for manufacturing and desired storage capacity. Unlike conventional high energy density electrical stroage devices such as batteries, the disclosed capacitor is extremely durable and can be operated at high frequencies (greater than 10 Hz).

The device disclosed is unlike a battery because the discharge voltage at constant discharge rate drops off linearly with discharge time. The disclosed device is superior to conventional double layer capacitors because the polymer is effectively a metal where every subunit is exposed to the electrolyte solution giving rise to a very high internal surface area.

Microcapacitors can be made using the same techniques as those used in fabricating the polymer-based transistors. These small sized, high energy devices have potential application in many areas since their capacitance is as much as 200 to 300 $J/cm^3$, compared to 1 $J/cm^3$ for conventional capacitors.

Figure 12:
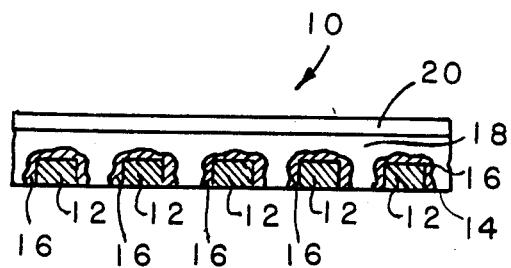
FIG. 12 is a cross-sectional view of a polymer-based electrochromic device.

As depicted in FIG. 12, an electrochromic device 10 which has very high resolution, responds rapidly, is stable over time, and which can be viewed from any angle is formed by derivatizing individually addressable microelectrodes 12 on an insulating substrate 14 wih polymer 16, overlaying the polymer-coated electrode with an electrolyte 18, providing a counter-electrode, and sealing in the electrolyte with a transparent cover 20. The advantages of the device over prior art displays include not only increased stability and rate of response but very high resolution since the individually coated microelectrodes can be spaced as closely as 10,000 Angstroms and the display can be viewed from any angle. A potential use for these devices is as a wrist-sized television screen.

The present invention may be embodied in other specific forms without departing from the spirit and scope thereof. These and other modifications of the invention will occur to those skilled in the art. Such other embodiments and modifications are intended to fall within the scope of the appended claims.

What is claimed is:

1. A microelectrochemical device comprising at least two electrically conductive electrodes, separated by less than two microns, on an inert insulating substrate overlaid with a conducting polymer polymerized from thiophene or derivatives of thiophene.

2. The device of claim 1 wherein said conducting polymer is selected from the group consisting of polythiophene, poly-3-methylthiophene and poly-3,4-dimethylthiphene.

3. The device of claim 2 comprising two electrodes formed of a metal and overlaid with the minimum thickness of poly-3-methylthiophene to connect two electrodes.

4. The device of claim 1 wherein the polymer further comprises a catalyst.

5. The device of claim 4 wherein the catalyst is selected from the group consisting of noble metals and enzymes.

6. The device of claim 5 wherein the noble metal is in the form of particles electrically insulated from each other when the polymer is not conducting.

7. An electrochromic device comprising one or more individually addressable, electrically conductive electrodes on an inert insulating substrate overlaid with a conducting polymer polymerized from thiophene or a derivative of thiophene, an electrolyte solution, a counter-electrode and an optically transparent material covering the electrolyte and polymer-overlaid electrodes, wherein said polymer-overlaid electrodes are separated by an approximate distance of up to one micron.

8. A polymer-based electrochemical device for storing electrical energy comprising two electrically conductive electrodes separated by less than two microns on an inert insulating substrate and an ionic conductor wherein said electrodes are coated with a polymer formed from thiophene or a thiophene derivative and separated by the ionic conductor.

9. The device of claim 8 wherein the polymer is highly conductive, exhibits a linear relationship between charge and potential within a desired range of potentials, has a high capacity for electrical charge per unit area of polymer, and can store and discharge energy at high frequencies.

10. The device of claim 9 wherein the polymer is durable in an aqueous solution.

11. The device of claim 9 wherein the polymer is selected from the group consisting of polythiophene, poly-3-methylthiophene, and poly-3,4-dimethylthiophene.

12. The device of claim 11 further comprising
an electrolyte solution, and
a housing which seals the electrolyte solution in the device adjacent the polymer and ionic conductor, wherein the polymer overlaying the electrodes is physically separated by the ionic conductor.

13. The device of claim 12 wherein the polymer layer is greater than 5 microns thick.

14. A method for sensing low magnitude chemical or electrical signals comprising:
providing a device including at least two electrically conductive electrodes separated by less than two microns on an inert insulating substrate, wherein said electrodes are overlaid with a polymer of thiophene or derivatives of thiophene, and
detecting signals by measuring changes in conductivity of said polymer that are a result of a change in the state of charge of said polymer which results in a net change in the concentration of ionic species in said polymer.

15. The method of claim 14 further comprising applying a potential of between 0.0 V and +1.4 V to said device and measuring changes in conductivity as changes in potential.

16. The method of claim 14 further comprising increasing the sensitivity of said device by decreasing the distance between said electrodes.

17. The method of claim 14 further comprising equilibrating said device with a reactant selected from the group of $O_2$, $H_2$, $I_2$ and other redox reagents and measuring changes in concentration of said reactants as changes in conductivity of said polymer.

18. The method of claim 14 further comprising contacting said device with a biological solution and measuring changes in blood components as a function of changes in conductivity of said polymer.

19. The method of claim 18 wherein the blood component is selected from the group consisting of $O_2$ and $H+(aq)$.

* * * * *